United States Patent [19]

Borow

[11] 4,315,369
[45] Feb. 16, 1982

[54] FOOD CUTTING AND GRASPING IMPLEMENT

[76] Inventor: Maxwell Borow, 73 Hillcrest Rd., Martinsville, N.J. 08836

[21] Appl. No.: 157,850

[22] Filed: Jun. 9, 1980

[51] Int. Cl.³ .............................................. B26B 13/00
[52] U.S. Cl. ......................................... 30/257; 30/148
[58] Field of Search ................ 30/145, 146, 148, 254, 30/257, 341; 128/318, 321

[56] References Cited
U.S. PATENT DOCUMENTS
2,136,414 11/1938 Clements .............................. 128/318

FOREIGN PATENT DOCUMENTS
16089 of 1906 United Kingdom .................. 30/148
136966 12/1919 United Kingdom .................. 30/148

Primary Examiner—Jimmy C. Peters
Attorney, Agent, or Firm—Robert A. Green

[57] ABSTRACT

The invention comprises a scissors having its cutting blades bend downwardly from the plane formed by the user's hand and the finger holes and operable with one hand to cut food into pieces and to grip a piece of food and direct it to the user's mouth.

3 Claims, 4 Drawing Figures

FOOD CUTTING AND GRASPING IMPLEMENT

BACKGROUND OF THE INVENTION

All over the world there are large numbers of people who have only one hand available for use in eating. At the present time, there is no satisfactory implement available which an individual can use with one hand to cut meat, grasp the meat and direct it to the mouth.

SUMMARY OF THE INVENTION

The invention comprises a pair of scissors having its cutting blades bent at an angle to the plane formed by the hand of the user and the finger holes. The method of the invention comprises grasping the scissors with the cutting blades facing down and using the cutting blades to cut a bite-size portion of food. The food is then grasped between the cutting blades, or associated structure, and it is directed into the user's mouth.

DESCRIPTION OF THE PREFERRED EMBODIMENTS

Figure 1:
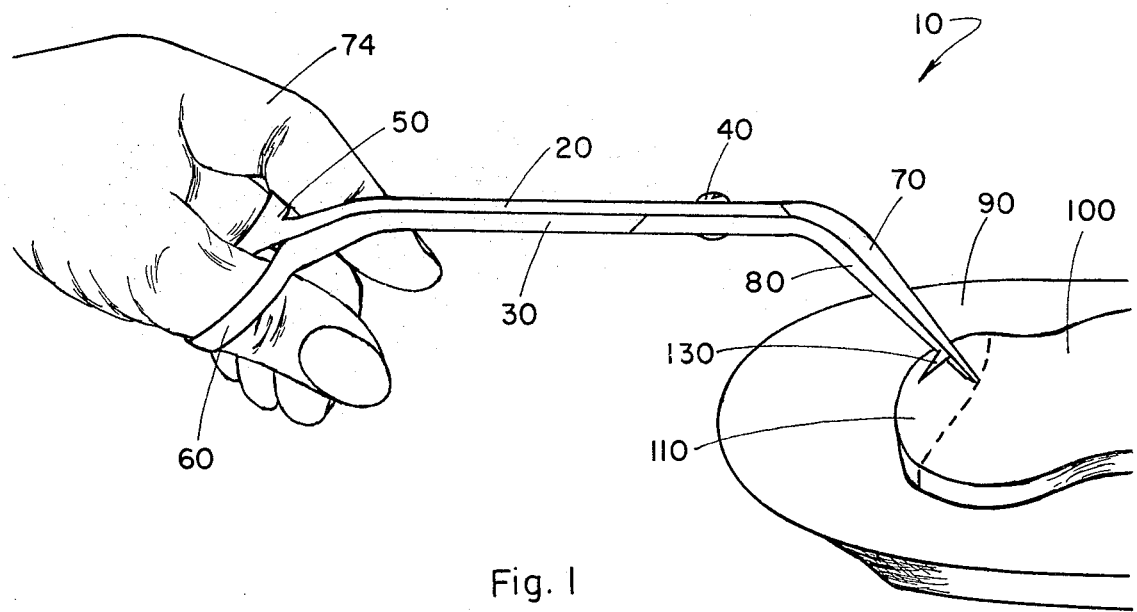
FIG. 1 is a side elevational view of the scissors of the invention and associated apparatus illustrating its use.

The apparatus of the invention 10 is generally in the form of a scissors having the usual two blades 20 and 30 which overlie each other and are pivotally connected together by a screw 40 or the like at a point intermediate their ends. Each blade has a finger hole at one end, blade 20 having a hole 50 and blade 30 having a hole 60. Each blade also has a cutting blade portion 70, 80 which makes up most of the length of the blade from the pivot point or screw 40 to its leading end. According to the invention, the cutting blade portions 70 and 80 are curved downwardly, still overlying each other, from the horizontal at a suitable angle, for the intended purpose to be described.

In addition, it is preferred that the finger-hole portions of the blades 20 and 30, rearward of pivot screw 40, are bent downwardly from the horizontal so that, in effect, the cutting blade portions 70 and 80 are disposed at about 90° to the horizontal. This permits optimum operation of the invention as described below. Portions of the blades 20 and 30 on both sides of pivot point 40 lie in what is considered to be the horizontal plane.

Figure 2:
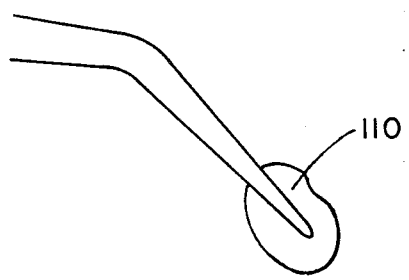
FIG. 2 is a side elevational view of a portion of the scissors of the invention showing the scissors grasping a morsel of food.
Figure 3:
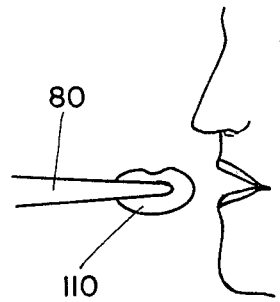
FIG. 3 is a side elevational view of a portion of the apparatus shown in FIG. 2 illustrating its use in placing food in the mouth.

According to the method of the invention, the user grasps the apparatus 10 with the thumb in one finger hole and the middle finger in the other hole, and with the cutting blades facing down and with the palm of the hand 74 facing down. Thus, the tip ends of the cutting blades face down toward a plate 90 on which there is food 100 to be cut and eaten. With the apparatus 10 thus oriented, the user operates the apparatus to cut a bite-size portion of food 110, and then he grasps the cut portion of food between the blades (FIG. 2) and raises it, and, by merely twisting his wrist, he inserts the food into his mouth (FIG. 3).

The apparatus 10 may be modified in various ways. For example, the tips of the cutting blades may be formed with one or more projecting teeth 120 (FIG. 4) which can be used like fork tines to pierce the cut piece of food and thus hold it as it is directed to the mouth. Alternatively, or in addition, one or more conical posts or tines 130, for piercing a bite of food, may be provided perpendicular to the flat surface of blade 20 or 30 at the leading end thereof (FIG. 1).

Figure 4:
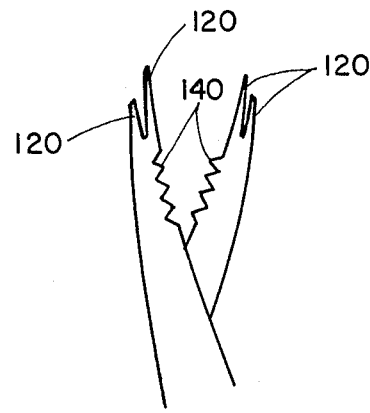
FIG. 4 is a view of the blades of a scissors illustrating a modification of the invention.

In another modification, the cutting edges of the blades 20 and 30 may be serrated, if desired, as illustrated in FIG. 4 at 140. Also, a spring (not shown) may be provided between the blades near the finger holes to facilitate opening of the blades.

To summarize or define the principles of the invention in other terms, considering that the blades of a scissors are normally thin flat overlying or abutting members which define a plane, then, according to the invention, the leading portions or cutting portions are curved, together, at an angle to that plane so that the cutting portions still maintain their abutting relationship. If the plane is considered to be horizontal, then the leading cutting portions are bent downwardly at an angle to the horizontal plane. In addition, it is desirable that the finger hole portions of the members are similarly bent at an angle to the horizontal plane, sloping downwardly to the horizontal and lying in a plane which slopes downwardly at an angle to the horizontal plane.

What is claimed is:

1. A scissors-like apparatus for use by a one-handed person to cut food and direct the cut food to the person's mouth comprising two blades pivotably coupled together and having parallel, overlying, generally central portions which lie in a first plane, said blades having a finger hole portion at one end of each, said blades having a bent portion and also having overlying cutting end portions which perform a cutting function and are located remote from said finger hole portions, said cutting end portions of said blades lying completely in a second plane which is bent at an angle to said first plane and extend to said bent portion whereby, when the central portions of said blades are disposed horizontally and spaced above a food plate during a food cutting operation, said cutting end portions slant downwardly toward and can touch a food plate and the cutting portions can be used to cut food and then grasp the cut food to bring it to the person's mouth.

2. The apparatus defined in claim 1 wherein said finger hole portions lie in a third plane which slopes downwardly at an angle to said first plane.

3. The apparatus defined in claim 1 wherein the cutting portions of the blades are, in effect, bent at an angle of about 90° to the horizontal.

* * * * *